(12) United States Patent
Mueller et al.

(10) Patent No.: US 9,523,670 B2
(45) Date of Patent: Dec. 20, 2016

(54) METHOD AND APPARATUS FOR DETERMINING HEMOGLOBIN BASED PARAMETERS IN AN UNLYSED BLOOD SAMPLE

(71) Applicant: Abbott Point of Care, Inc., Princeton, NJ (US)

(72) Inventors: Cord Mueller, Madison, CT (US); Stephen C. Wardlaw, Lyme, CT (US); Darryn W. Unfricht, North Haven, CT (US)

(73) Assignee: Abbott Point of Care, Inc., Princeton, NJ (US)

( * ) Notice: Subject to any disclaimer, the term of this patent is extended or adjusted under 35 U.S.C. 154(b) by 208 days.

(21) Appl. No.: 14/274,269

(22) Filed: May 9, 2014

(65) Prior Publication Data

US 2014/0334712 A1   Nov. 13, 2014

Related U.S. Application Data

(60) Provisional application No. 61/879,976, filed on Sep. 19, 2013, provisional application No. 61/821,448, filed on May 9, 2013.

(51) Int. Cl.
*G06K 9/00* (2006.01)
*G01N 33/49* (2006.01)
(Continued)

(52) U.S. Cl.
CPC .............. *G01N 33/49* (2013.01); *G01N 15/06* (2013.01); *G01N 21/03* (2013.01);
(Continued)

(58) Field of Classification Search
CPC .. G01N 15/05; G01N 2015/055; G01N 33/49; G06T 7/0012
(Continued)

(56) References Cited

U.S. PATENT DOCUMENTS 5,812,419 A * 9/1998 Chupp ............... G01N 35/1004
                                                      702/20
6,519,025 B2 * 2/2003 Shepherd ............... G01N 21/31
                                                      356/39

(Continued)

OTHER PUBLICATIONS

International search report for PCT/US2014/037516 dated Sep. 19, 2014.

*Primary Examiner* — Tom Y Lu
(74) *Attorney, Agent, or Firm* — O'Shea Getz P.C.

(57) ABSTRACT

A method and apparatus for determining hemoglobin concentration is provided. A method aspect includes the steps of: a) depositing an unlyzed, substantially undiluted blood sample into an analysis chamber adapted to quiescently hold the sample for analysis; b) imaging the sample in a region of the analysis chamber where the height of the chamber is no more than about twenty microns ($20\mu$) or no less than about two microns ($2\mu$), to produce image signals representative of the optical density of the imaged region; c) determining a sample representative optical density value using the image signals representative of the optical density of the imaged region; and d) determining the hemoglobin concentration of the sample using the sample representative optical density value.

20 Claims, 2 Drawing Sheets

(51) Int. Cl.
  *G01N 21/03* (2006.01)
  *G01N 21/59* (2006.01)
  *G01N 15/06* (2006.01)
  *G01N 21/31* (2006.01)
  *G01N 15/00* (2006.01)

(52) U.S. Cl.
  CPC ..... *G01N 21/5907* (2013.01); *G06K 9/00134* (2013.01); *G01N 2015/0065* (2013.01); *G01N 2021/0346* (2013.01); *G01N 2021/3144* (2013.01); *G01N 2333/805* (2013.01)

(58) Field of Classification Search
  USPC .................................................. 382/128, 134
  See application file for complete search history.

(56) References Cited

U.S. PATENT DOCUMENTS

| | | | |
|---|---|---|---|
| 6,718,190 B2 * | 4/2004 | Krivitski | A61B 5/1495 600/322 |
| 2009/0238438 A1 | 9/2009 | Wardlaw et al. | |
| 2010/0189338 A1 | 7/2010 | Lin et al. | |
| 2011/0136152 A1 | 6/2011 | Lin et al. | |
| 2012/0021456 A1 | 1/2012 | Levine et al. | |
| 2012/0262703 A1 | 10/2012 | Zahniser et al. | |

* cited by examiner

METHOD AND APPARATUS FOR DETERMINING HEMOGLOBIN BASED PARAMETERS IN AN UNLYSED BLOOD SAMPLE

This application claims priority to U.S. Patent Appln. No. 61/879,976 filed Sep. 19, 2013 and U.S. Patent Appln. No. 61/821,448 filed May 9, 2013.

BACKGROUND OF THE INVENTION

1. Technical Field

The present invention relates to apparatus and methods for analysis of whole blood samples in general, and for the determination of certain hemoglobin based parameters, such as hemoglobin concentration, of an unlysed, undiluted whole blood sample in particular.

2. Background Information

Physicians, veterinarians and scientists have examined human and animals' biologic fluids, especially blood, in order to determine constituent particulate quantities as well as to identify the presence of unusual particulates not seen in healthy subjects. The particulates generally measured, quantified and identified include red blood cells (RBCs), white blood cells (WBCs), and platelets. RBC analyses can include determinations of RBC number, hemoglobin concentration, and hematocrit (also referred to as the packed cell volume).

In many prior art applications, the hemoglobin concentration of a blood sample is determined by first lysing the RBCs within the sample, and subsequently determining the hemoglobin concentration of the sample containing the lysed RBCs. A distinct disadvantage of lysing the RBCs is that once the RBCs are lysed, it is no longer possible to perform cellular analyses on RBCs in the aforesaid sample; e.g., RBC cell volume (CV), mean cell volume (MCV), cell hemoglobin concentration (CHC), mean cell hemoglobin concentration (MCHC), mean cell hemoglobin content (MCH), etc.

SUMMARY OF THE INVENTION

According to an aspect of the present invention, a method for determining red blood cell hemoglobin concentration is provided that includes the steps of a) depositing an unlysed, substantially undiluted blood sample into an analysis chamber adapted to quiescently hold the sample for analysis, the chamber defined by an interior surface of a first panel, and an interior surface of a second panel, wherein both panels are transparent, and which chamber has a height extending between the interior surface of the first panel and the interior surface of the second panel; b) imaging the sample in a region of the analysis chamber where the height of the chamber is no more than about twenty microns (20μ) or no less than about two microns (2μ), to produce image signals representative of the optical density of the imaged region; c) determining a sample representative optical density value using the image signals representative of the optical density of the imaged region; and d) determining the hemoglobin concentration of the sample using the sample representative optical density value.

According to another aspect of the present invention, a method for determining red blood cell hemoglobin concentration is provided that includes the steps of: a) depositing an unlysed, substantially undiluted blood sample into an analysis chamber adapted to quiescently hold the sample for analysis; b) imaging the sample in a region of the analysis chamber to produce image signals representative of the optical density of the imaged region; c) determining a sample representative optical density value using the image signals; and d) determining the hemoglobin concentration of the sample using the sample representative optical density value.

According to another aspect of the present invention, an apparatus for determining red blood cell hemoglobin concentration within an unlysed, substantially undiluted whole blood sample is provided. The apparatus includes an analysis chamber, a sample illuminator, an image dissector, and an analyzer. The analysis chamber is adapted to quiescently hold the sample for analysis. The chamber is defined by an interior surface of a first panel, and an interior surface of a second panel, wherein both panels are transparent. The chamber has a height extending between the interior surface of the first panel and the interior surface of the second panel, which height is no more than about twenty microns (20μ) or no less than about two microns (2μ). The sample illuminator is adapted to emit light to pass through the sample quiescently residing within the chamber. The image dissector is adapted to capture light originating from the sample illuminator and passed through the sample quiescently disposed within the chamber. The image dissector is further adapted to produce image signals representative of the light passed through the sample. The analyzer is adapted to determine a sample representative optical density value using the image signals, and to determine the hemoglobin concentration of a region of the sample using the sample representative optical density value.

The present method and advantages associated therewith will become more readily apparent in view of the detailed description provided below, including the accompanying drawings.

DETAILED DESCRIPTION OF EMBODIMENTS OF THE INVENTION

The present method and apparatus for analyzing a sample of unlysed and substantially undiluted whole blood sample allows the determination of the hemoglobin based parameters including, but not limited to, hemoglobin concentration, hematocrit and red blood cell (RBC) count, without the addition of any dyes, reagents (other than anticoagulants in some embodiments) or diluents to the sample.

The present method utilizes an analysis chamber that is operable to quiescently hold a sample of unlysed and substantially undiluted whole blood for analysis. As will be explained below the sample is typically, but not necessarily, anti-coagulated. The chamber is typically sized to hold about 0.2 to 1.0 μl of sample, but the chamber is not limited to any particular volume capacity, and the capacity can vary to suit the analysis application. The phrase "substantially undiluted" as used herein describes a blood sample which is either not diluted at all or has not been diluted purposefully, but has had some reagents added thereto for purposes of the analysis. To the extent the addition of the reagents dilutes the sample, if at all, such dilution has no clinically significant impact on the analysis performed. Typically, the only reagents that will be used in performing the present method are anti-coagulants (e.g., EDTA, heparin) and in some instances, an isovolumetric sphering agent. These reagents are generally added in dried form and are not intended to dilute the sample. Under certain circumstances (e.g., very rapid analysis), it may not be necessary to add the anti-coagulating agent, but it is preferable to do so in most cases to facilitate analyses of the sample. The term "quiescent" is used to describe that the sample is deposited within the chamber for analysis, and the sample is not purposefully moved relative to the chamber during the analysis; i.e., the sample resides quiescently within the chamber. To the extent that motion is present within the blood sample, it will predominantly be due to Brownian motion of the blood sample's formed constituents, which motion is not disabling of the use of the device of this invention.

Figure 1:
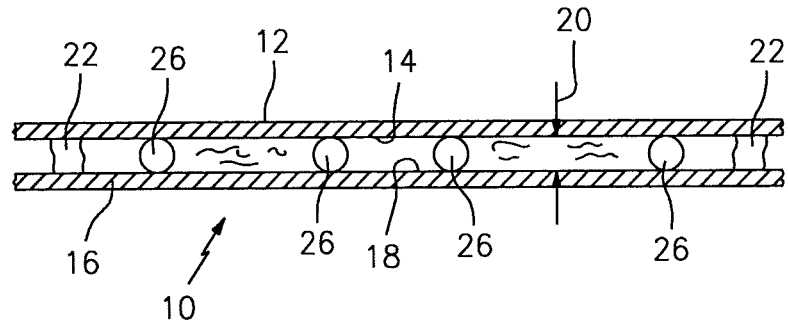
FIG. 1 is a cross-sectional diagrammatic representation of an analysis chamber that may be used in the present method.

Referring to FIG. 1, in some embodiments the analysis chamber 10 is a void defined by an interior surface 14 of a first panel 12, and an interior surface 18 of a second panel 16. The panels 12, 16 are both sufficiently transparent to allow the transmission of light along predetermined wavelengths there through in an amount sufficient to perform the optical density analysis described below. Preferably, at least a portion of the panels 12, 16 are parallel with one another, and within that portion the interior surfaces 14, 18 are separated from one another by a height 20. The present method can utilize a variety of different analysis chamber types having the aforesaid characteristics, and is not therefore limited to any particular type of analysis chamber. An analysis chamber having parallel panels 12, 16 simplifies the analysis and is therefore preferred, but is not required for the present invention; e.g., a chamber having one panel disposed at a known non-parallel angle relative to the other panel could be used. For human blood analyses, the height 20 of the chamber 10 is typically no more than twenty microns (20μ) and no less than two microns (2μ), and is preferably about four microns (4μ). As will be explained below, the thin layer of sample created in such a narrow height chamber 10 provides imaging and analysis advantages. An analysis chamber that includes a single panel onto which the sample is deposited can also be used.

In the analysis chamber 10 embodiment shown in FIG. 1, the analysis chamber 10 is further defined by one or more lateral boundaries 22 that contain the lateral spread of the sample between the interior surfaces 14, 18; e.g., a lateral boundary 22 may be formed by a hydrophobic coating applied to one or both interior surfaces 14, 18, or by a bead of adhesive (or other formable) material extending between the interior surfaces 14, 18, or by a physical configuration that stops lateral capillary flow of the sample. A bead of adhesive material provides the advantage of also attaching the first panel 12 to the second panel 16. Lateral boundaries 22 are not required under the present invention.

In some embodiments, the chamber 10 may include a plurality of separators 26 disposed between the panels 12, 16, within the chamber 10. The separators 26 can be any structure that is disposable between the panels 12, 16, operable to space the panels 12, 16 apart from one another. The dimension of a separator 26 that extends between the panels 12, 16 is referred to herein as the height of the separator 26. The heights of the separators 26 typically do not equal one another exactly (e.g., manufacturing tolerances), but are within commercially acceptable tolerance for spacing means used in similar analysis apparatus. Spherical beads are an example of an acceptable separator 26 and are commercially available from, for example, Bangs Laboratories of Fishers, Ind., U.S.A.

In some embodiments, the separators 26 may consist of a material that has greater flexibility than one or both of the first panel 12 and the second panel 16; e.g., capillary forces acting on the panels 12, 16 when sample resides in the chamber 10 cause larger separators 26 to compress to the point where most separators 26 are touching the interior surfaces 14, 18 of the panels 12, 16, thereby making the chamber height 20 just slightly less than the mean separator 26 diameters. In some embodiments, the separators 26 may consist of a material that has less flexibility than one or both of the first panel 12 and the second panel 16. For example, the first panel 12 may be formed from a material more flexible than the separators 26 and the second panel 16. In response to capillary forces acting on the panels 12, 16, the first panel 12 will bend and overlay in a tent-like fashion certain separators 26 having a greater than average height. In this embodiment, although small local regions of the chamber 10 may deviate from the desired chamber height 20, the average height 20 of the chamber 10 will be very close to that of the mean separator 26 diameter. Analysis indicates that the mean chamber height 20 can be controlled to one percent (1%) or better at chamber heights of less than four microns (4μ) using this embodiment. Subject to the flexibility characteristics described above (as well as other factors such as the distribution density of the separators), the separators 26 and panels 12, 16 can be made from a variety of materials, provided the panels 12, 16 are sufficiently transparent. Transparent plastic films consisting of acrylic or polystyrene are examples of acceptable panels 12, 16, and spherical beads made of polystyrene, polycarbonate, silicone, and the like, are acceptable separators 26. A specific example of an acceptable separator is spheres made of polystyrene that are commercially available, for example, from Thermo Scientific of Fremont, Calif., U.S.A., catalogue no. 4204A, in four micron (4 μm) diameter. This example of an acceptable analysis chamber 10 is described in greater detail in U.S. patent application Ser. Nos. 12/971,860; 13/341,618; and 13/594,439; and U.S. Pat. Nos. 7,903,241; 7,929,122; and 7,951,599, each of which is hereby incorporated by reference in its entirety.

The height 20 of the chamber 10 can alternatively be determined as a part of the manufacturing process of the chamber 10 and provided with the chamber, or can be determined using a variety of techniques including the use of a known quantity of sensible colorant, or the use of geometric characteristics disposed within the chamber 10, that can be used to determine the volume of sample for a known field area, and consequently the height of the chamber 10. These techniques and others are described in U.S. Pat. Nos. 6,723,290 and 6,929,953. The present invention is not limited to these techniques, however.

In some applications, an isovolumetric sphering agent (e.g., a zwitterionic detergent or similarly functioning reagent) may be admixed with at least a portion of the sample to cause at least some of the RBCs to assume a substantially spherical geometry, rather than the bioconcave disc shape they typically assume in nature. The isovolumetric sphering agent may be disposed in a portion, or all, of the chamber 10 (e.g., by deposition on an interior surface), or elsewhere in a cartridge including the chamber 10.

Figure 2:
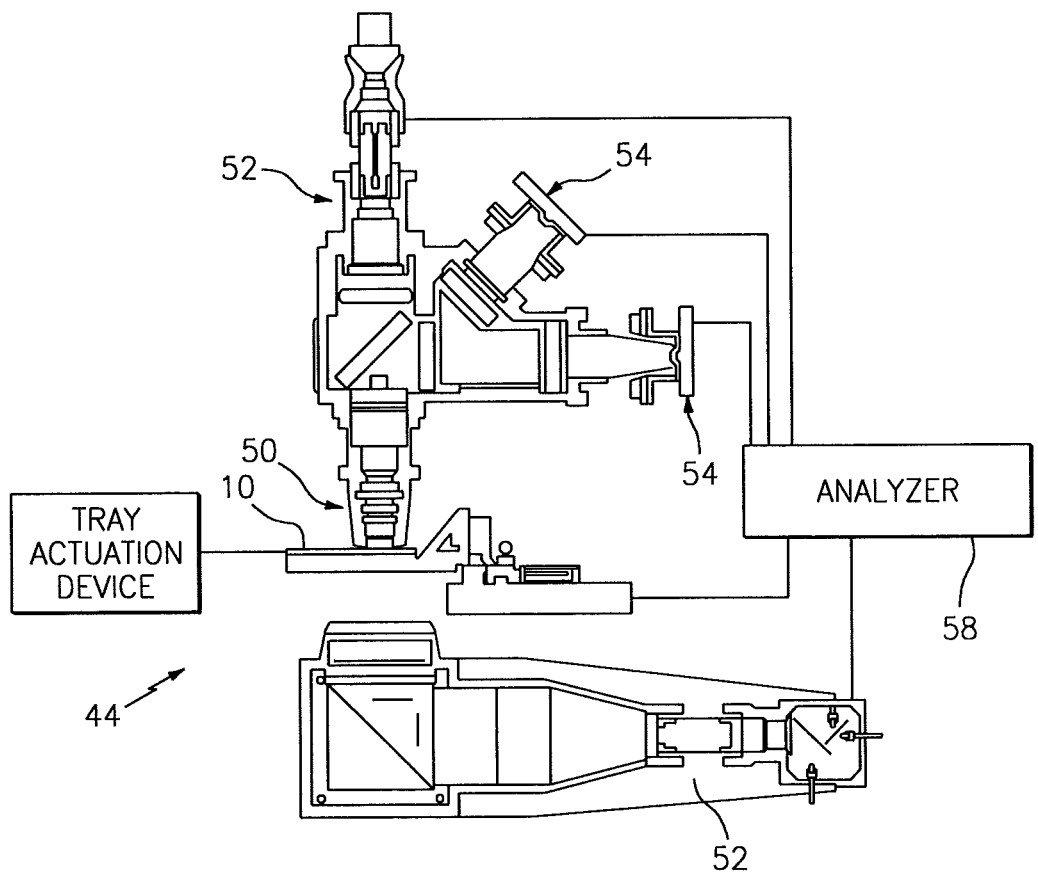
FIG. 2 is a diagrammatic schematic of an analysis device that may be used with the present method.

Referring to FIG. 2, the analysis of the sample quiescently disposed within the chamber 10 is performed using an analysis device 44 that is operable to image at least a portion of the sample and perform an analysis on the image. The image is produced in a manner that permits the optical density of sample to be determined on a per unit basis. The term "per unit basis" or "image unit" means a defined incremental unit of which the image of the sample can be dissected. A pixel, which is generally defined as the smallest element of an image that can be individually processed within a particular imaging system, is an example of an image unit, and an image unit may also include a small number of pixels in a collective unit. The magnification of an analysis device 44 can also be described in linear terms (e.g., microns per pixel at the focal plane), where the linear dimension is along a particular axis of an orthogonal grid applied to the image. The actual area of the sample captured by pixels (or other image units) of the sensor at the focal plane is therefore a function of the magnification factor applied by the analysis device 44. Hence, the magnification of the analysis device 44 is typically known or determinable. The volume associated with that pixel is therefore the area of the image per pixel times the known/determinable chamber height 20. For example if the magnification was 0.5 microns per pixel, an image occupying 200 pixels would have an area of 50 square microns, and a volume of 50 square microns times the chamber height 20.

A specific example of an analysis device 44 that can be adapted for use with the present method is shown in FIG. 2. This specific analysis device 44 is described hereinafter for illustrative purposes, and the present invention is not limited to this particular device. The analysis device 44 includes at least one sample illuminator 52, at least one image dissector 54, and an analyzer 58 (e.g., a programmable analyzer). The sample illuminator 52 includes a light source that selectively produces light at particular wavelengths within a wavelength range broad enough to be useful for the analyses described herein (e.g., wavelengths within the range of about 400-670 nm; light at or about 413 nm and at or about 540 nm is particularly effective in determining the optical density of the hemoglobin within a sample of human blood in view of the high light absorption that occurs within the hemoglobin at the aforesaid wavelengths, which is reflected in the high molar extinction coefficient (c) at the aforesaid wavelengths). The sample illuminator 52 typically includes optics for manipulating the light. In certain preferred embodiments, the light source includes a plurality of light-emitting diodes (LEDs). By their nature, LEDs produce light along a relatively narrow spectral emission profile, with a peak intensity located at a particular wavelength (i.e., the "peak wavelength" of the LED). In those embodiments of the present invention that utilize a light source including a plurality of LEDs, the LEDs produce light at different peak wavelengths; e.g., an LED with a peak wavelength at or about 413 nm, another LED with a peak wavelength at or about 540 nm, etc. For the imaging analyses provided below that involve determining the OD of a sample, the "sample representative OD value" (defined below) is determined using light at a single wavelength, which in those embodiments that use an LED light source would be the peak wavelength of the LED being used.

The analysis device 44 utilizes transmittance to produce an image. The light transmission properties of the sample can be measured, for example, by directing light from the sample illuminator 52 to pass through the sample quiescently disposed between chamber panels 12, 16, and thereafter capturing the light using the image dissector 54. The image dissector 54 is operable to create signals on a per image unit basis and pass those signals to the analyzer 58 for processing. An example of an acceptable image dissector 54 is a charge couple device (CCD) type image sensor that converts the light passing through the sample into an electronic data format. Complementary metal oxide semiconductor ("CMOS") type image sensors are another example of an image sensor that can be used, and the present invention is not limited to either of these examples.

The analyzer 58 includes a central processing unit (CPU) and is in communication with the sample illuminator 52 and image dissector 54. The analyzer 58 is adapted (e.g., programmed) to selectively perform the functions necessary to perform aspects of the present invention, including: 1) perform the instructions of a computer program: 2) perform basic arithmetical and/or logical functions; and 3) perform input/output operations of the analyzer, etc. For example, the analyzer 58 is adapted to send signals to, and receive signals from, the sample illuminator 52 and the image dissector 54, selectively perform the functions necessary to operate the sample illuminator 52 and the image dissector 54, and process the signals (e.g., from the image dissector 54) to perform the analyses described herein. The analyzer 58 is not limited to interacting with the sample illuminator 52 and the image dissector 54; e.g., in the embodiment shown in FIG. 2, the analyzer is also adapted to control a tray actuation device operable to move the analysis chamber 10 relative to an objective lens 50 of the analysis device 44. A person skilled in the art would be able to adapt (e.g., program) the analyzer 58 to perform the functionality described herein without undue experimentation. The analysis devices described in U.S. Pat. No. 6,866,823 and U.S. patent application Ser. Nos. 13/077,476 and 13/204,415 (each of which is hereby incorporated by reference in its entirety) are examples of acceptable types of an analysis device 44 adaptable for use with the present methods. Aspects of the present invention are not limited to use with these analysis devices, however. It should be noted that the functionality of analyzer 58 may be implemented using hardware, software, firmware, or a combination thereof.

The analysis device 44 is adapted to determine an OD value associated with the detected light signal on a per image unit basis for an imaged region of the sample; e.g., which region includes the whole blood sample and is not limited to RBCs within the sample. The determined OD of the sample is a function of the hemoglobin concentration within the sample, the molar extinction coefficient (also referred to as molar absorptivity) for hemoglobin at a given wavelength, and the distance of the light path traveled through the hemoglobin and can be represented by the following relationship:

$$OD = \epsilon c L$$

where $\epsilon$=hemoglobin molar extinction coefficient, c=hemoglobin concentration, and L=distance traveled through the hemoglobin within the sample between the panel interior surfaces 14, 18. The molar extinction coefficient is an intrinsic property of the hemoglobin that can be can be derived by experimentation, or through empirical data currently available.

In the determination of certain hemoglobin based parameters, the OD is determined by the analyzer 58 and the hemoglobin molar extinction coefficient (c) is known. The OD is determined on a per image unit basis (e.g., per pixel) for a region (or all) of the sample quiescently residing within the analysis chamber 10 which is being analyzed; e.g., which region includes the whole blood sample and is not limited to RBCs within the sample region. As indicated above, the sample residing within the chamber 10 is unlysed and substantially undiluted. Some number of the determined per image unit OD values are subsequently statistically analyzed by the analyzer 58 and a value representative of the individual image unit OD values (e.g., an average value) is determined, which representative value is referred to hereinafter as the "sample representative OD value". The number of determined per image unit OD values used to determine the sample representative OD value can vary depending upon the application. For increased accuracy sake, the number of determined per image unit OD values used to determine the sample representative OD value is preferably substantially all of the determined per image unit OD values within the sample analysis region. However, in some instances it may be desirable to "filter" the determined per image unit OD values to eliminate outlier values, or other such values that may negatively affect the accuracy of the data. Alternatively, in some applications it may be possible to get valid data using less than all of the determined per image unit OD values, which fewer values can decrease computing requirements and time. The sample representative OD value may be subsequently evaluated directly or indirectly relative to empirical data to determine a hemoglobin based parameter, for example, a hemoglobin concentration value of the sample. Alternatively, the sample representative OD value may be subsequently evaluated directly or indirectly relative to a theoretical or analytical model that takes into account the power spectrum of the light source (e.g., an LED) as a function of wavelength and the responsivity of the image dissector to determine a hemoglobin based parameter, for example, a hemoglobin concentration value of the sample.

The hemoglobin concentration of the sample may be determined using the sample representative OD value and empirical data. For example, the analyzer 58 may be adapted to include empirical data that relates OD values to hemoglobin concentration. In one embodiment, the empirical data may include OD values and corresponding hemoglobin concentration values based on a clinically significant number of samples previously tested; e.g., "N" number of samples, where "N" is an integer). For example, the empirical data may have been produced on the aforesaid clinically significant number of samples using devices/techniques for determining OD values and hemoglobin concentration values, which devices/techniques are established and known in the art to produce accurate data; e.g., capable of producing standard reference values. The corresponding "reference" OD and hemoglobin concentration values (i.e., empirical data) may be organized in several different forms that can then be used with the sample representative OD value determined by the analyzer 58 to determine the hemoglobin concentration of the sample being analyzed. For example, the empirical data could be arranged in a graphical solution wherein a Y-axis of a graph represents the OD values, and an X-axis of the graph represents the hemoglobin concentration values, and the empirical data is then plotted as a function of the two axes. A linear solution can be derived from the plotted data, which is representative of the plotted data; e.g., in a "y=mx+b" format. Once the linear solution of the empirical data is determined, that linear solution can then be used to determine a hemoglobin concentration value corresponding to the determined sample representative OD value from the sample being analyzed. The graphical solution described here is an example of how the hemoglobin concentration of a particular sample may be determined using empirical data. The present invention is not limited to this example, however. For example, in an alternative approach, the empirically produced data can be used to create a look-up table, which table can be used to determine a hemoglobin concentration value corresponding to a determined sample representative OD value.

Figure 3:
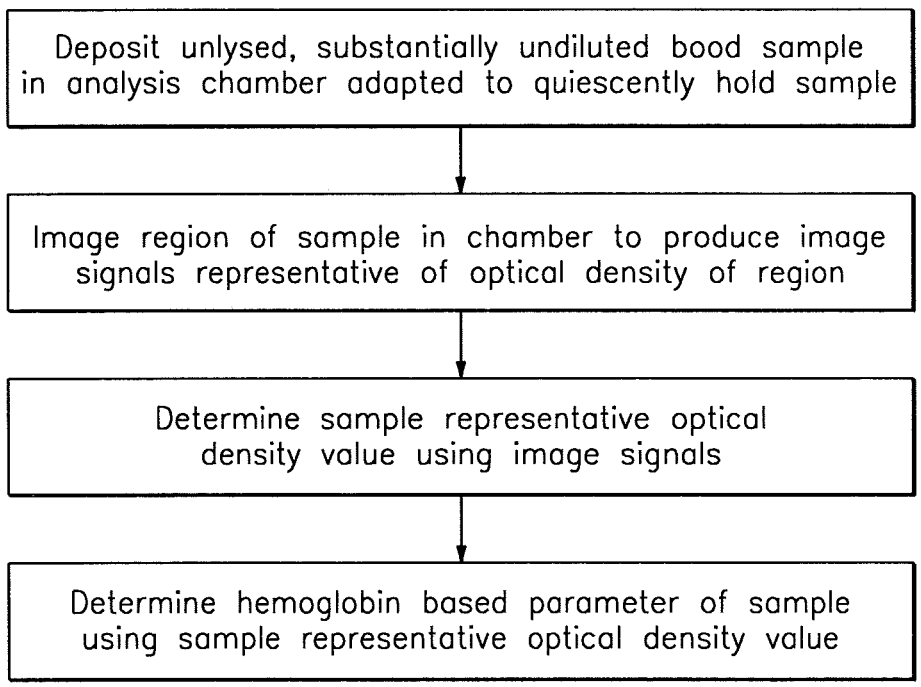
FIG. 3 is a block diagram illustrating method steps for determining a hemoglobin based parameter of an unlysed, substantially undiluted whole blood sample according to an aspect of the present invention.

Referring to FIGS. 1-3, to illustrate aspects of the present method, or an apparatus using the described methodologies, the following example for determining the hemoglobin concentration of the sample is provided. A sample of unlysed, substantially undiluted whole blood is placed in a chamber 10 as is described above, and thereafter quiescently resides within the chamber 10 during the imaging. In some instances, one or both of an anti-coagulating agent and an isovolumetric sphering agent may be mixed with the sample either prior to its introduction into the chamber 10 or upon introduction into the chamber 10.

At least a portion of the unlysed, substantially undiluted sample quiescently residing within the chamber 10 is imaged using the analysis device 44; e.g., by transmitting light (e.g., at or about 413 nm) from a sample illuminator 52 through the sample, and detecting such transmitted light passing through the sample by an image dissector 54. As indicated above, it is not a requirement that the entire sample residing within the chamber 10 be imaged, but may be preferable; e.g., in instances when the distribution of RBCs within a chamber 10 is likely to be non-homogeneous for a sample of unlysed, substantially undiluted whole blood. OD values are determined on a per image unit basis (e.g., per pixel) by the analyzer 58 for some or all the sample quiescently residing within the analysis chamber 10. Also as indicated above, the OD values determined on a per image unit basis portion of the sample reflect the whole blood sample in the region imaged, and are not limited to the RBCs in the aforesaid region; i.e., the OD values are not determined on a cellular basis. The determined per image unit OD values are subsequently statistically analyzed and a value representative of the individual image unit OD values (e.g., an average value) in the region is determined by the analyzer 58, which value is referred to herein as the "sample representative OD value". The sample representative OD value is subsequently evaluated directly or indirectly relative to empirical data (e.g., using the linear solution described above, or a look-up table, etc.) to determine the hemoglobin concentration value of the sample, which value is determined in units of grams per deciliter (g/dl) in the known or determinable volume of the sample within the chamber 10.

The above described OD imaging of the sample will capture all of the constituents within the sample; e.g., RBCs in their normal bioconcave form, spherized RBCs if a spherizing agent is added to the sample, white blood cells (WBCs), reticulocytes, etc. In some embodiments, the analyzer 58 may be adapted to mask the image portion of certain elements from the image used to determine the per image unit OD values, leaving the remainder of the sample for analysis purposes. For example, for certain analyses it may be desirable to mask the image portions attributable to WBCs, and/or those image portions attributable to reticulocytes, and/or those image portions attributable to separators 26 disposed within the sample. If masking is used, the masked image can then be used to determine the per image unit OD values, and in turn determine the sample representative OD value and the desired hemoglobin based parameter; e.g. hemoglobin concentration. As indicated above, the present invention is operable to determine the hemoglobin based parameters in the manner described above on samples having RBCs in their natural bioconcave form, or on spherized RBCs, or both; e.g., the described aspects of the present invention are operable regardless of whether there are RBCs in contact with the interior surfaces of the analysis chamber 10 or not.

For those chamber embodiments that include a first panel and a second panel, the above described chamber height 20 of no more than twenty microns (20µ) and no less than two microns (2µ), and preferably about four microns (4µ) for human blood analysis, is chosen to facilitate the determination of the hemoglobin based parameters described herein as well as others. The aforesaid chamber height 20 limits the sample layer to essentially a monolayer of the constituents within the chamber 10 (particularly at the four micron (4µ) height). The thin sample layer facilitates accurate imaging and subsequent analysis with minimal or no need to accommodate light scattering effects, or potential interference from non-RBC constituents within any particular light path, when acquiring the OD images. As a result, the analyses are simplified (e.g., no need to manipulate the image data to address light scattering), with concomitant greater possible accuracy.

The above description of aspects of the present invention details embodiments operable to determine a hemoglobin concentration. The present invention is not limited to this particular aspect and can be used to determine other hemoglobin based parameters. For example, aspects of the present invention can be used to determine the hematocrit of the sample, or to determine a RBC count of the sample. U.S. Pat. Nos. 7,903,241 and 7,929,241 ("Method and Apparatus for Determining Red Blood Cell Indices of a Blood Sample Utilizing the Intrinsic Pigmentation of Hemoglobin Contained Within the Red Blood Cells"), which are incorporated by reference above, describe methods and apparatus for determining cellular RBC indices such as mean cell hemoglobin content (MCH) and means cell hemoglobin concentration (MCHC). Aspects of the present invention can use these cellular based values and the hemoglobin concentration (Hgb) of the sample, determined pursuant to aspects of the present invention described herein, to determine the hematocrit (Hct) or the RBC count of the sample. For example, the hematocrit of the sample can be determined as follows:

$$Hct = \frac{Hgb}{MCHC}$$

The RBC count of the sample can be determined as follows:

$$RBC\ Count = \frac{Hgb}{MCH}$$

These hemoglobin based parameters and the method for determining them are illustrative of the information available using aspects of the present invention, and the present invention is not limited to these examples. These aspects of the present invention are also illustrative, however, of some of the significant advantages of the present invention. For example, the ability of the present invention to determine hemoglobin based parameters such as hemoglobin concentration in an unlysed whole blood sample quiescently residing within a thin chamber 10 (e.g., no more than 20 microns (20µ) and no less two microns (2µ) permits a multitude of analyses to be performed on a sample that would not be possible if the RBCs in the sample were lysed; e.g., RBC information on a cellular level within the sample is still available.

As indicated above, aspects of the present invention can be used to determine hemoglobin based parameters other than the hemoglobin concentration. For example, for certain analyses it may be desirable to determine RBC cell volume values (e.g., individual RBC volumes, mean RBC cell volumes, red blood cell distribution width (sometimes referred to as "RDW"), etc.). Methods for determining the volume of a RBC are disclosed in U.S. Pat. No. 7,903,241 (incorporated by reference above) and U.S. Patent Pub. No. 2011/0164803, which is hereby incorporated by reference in its entirety.

In the '241 patent, a method of determining the volume of an RBC, or the mean volume of a number of RBCs, includes determining the per image unit OD values for the RBCs under consideration, and determining a mean maximal OD value of a number of RBCs; e.g., a statistically sufficient number of RBCs in contact with the interior surfaces 14, 18 of both panels 12, 16 of the chamber 10. The RBC cell volume can be determined by integrating the volume of the RBC as a function of the OD of the hemoglobin within the RBC. The chamber area represented by each image unit is determined, and the volume associated with that image unit is therefore the area of the image unit times the known chamber height. Alternatively, the cell volume can be determined by dividing the individual RBC into different volumetric portions: a portion that contacts both surfaces ("Region I"), and a portion that does not contact both or even one of the interior surfaces ("Region II"). The volume of the cell portion in contact with the interior surfaces is determined by sensing the OD of that portion (i.e., Region I). The OD is sensed and is defined on a per image unit basis. As indicated above, the chamber area represented by each image unit is determined, and the volume associated with that image unit is therefore the area of the image unit times the known chamber height. The volume of the RBC portion in touch with both surfaces (i.e., Region I) is, therefore, equal to the sum of the volumes associated with each image unit within the two-surface contact area. The volume of the portion of the RBC not in contact with both surfaces (i.e., Region II) can be determined in a similar manner; e.g., as a percentage of the volume based on the determined image unit OD values. Since the hemoglobin molar extinction coefficient ($\epsilon$) is a linear function, the relative OD value of each pixel within Region II also represents the height of the RBC 22 associated with that image unit. The volume associated with each image unit in Region II is determined on a per image unit basis and is summed to determine the volume in Region II of the RBC. The volume of the individual RBC is the sum of Regions I and II. For those RBCs not contacting both interior surfaces (or if the chamber has only one panel), the cell volume can be determined using the previously obtained mean maximal optical density of the RBCs that are in contact with both interior surfaces, or using empirically determined data.

The '803 Publication discloses a method for determining a cell volume of an RBC within a blood sample that utilizes geometric modeling based on a per image unit OD value profile. An unlysed whole blood sample is deposited into an analysis chamber having first and second panels with interior surfaces separated by one another by a height. An RBC is imaged to determine the per image unit OD values, and representative image signals are produced. A radius of an RBC is determined using the per image unit OD values, and the volume of the imaged red blood cell is determined using the determined radius.

Regardless of how individual RBC volumes are determined, the mean cellular volume ("MCV") for RBCs within the sample can be determined using the individual cell volume values determined for a statistically significant number of RBCs and statistically analyzing the individual cell volumes to determine a mean and a measure of the accuracy or confidence of the mean; e.g., an acceptable standard deviation of the mean. The number of individual RBC cell volume values needed to determine a MCV with an acceptable measure of accuracy will depend on the RBC population analyzed, which number can range from about a few hundred to several thousand RBCs.

The RBC volumes, and the MCV value and associated statistical information can also be used to determine the red blood cell distribution width (often referred to as the "RDW" or "RCDW"). The RDW is a statistical measure of the volumetric variation of RBCs. Certain biologic disorders (e.g., a deficiency of Vitamin $B_{12}$, etc.) can cause an elevated RDW value. Mathematically, the RDW value can be determined as follows:

RDW=(Standard deviation of cell volumes÷MCV)× 100

The above described methodologies for determining the individual RBC volumes, the MCV, the mean MCV, and the standard deviation of the MCV are examples of acceptable methodologies, and the present invention is not limited to these specific techniques.

For example, a methodology for determining OD values on a per image unit basis (e.g., per pixel) for a region (or all) of the sample quiescently residing within the analysis chamber 10 (or a single panel chamber) which is being analyzed as described above, including the determination of a sample representative OD value. The aforesaid per image unit OD values can be used to determine the volume of individual RBCs. For example, the per image unit OD values for a region of sample will vary from those values associated with only plasma (i.e., no RBC or other constituent), to those per image OD values associated with a linear path completely occupied by a RBC (e.g., a spherized RBC). Individual RBCs can be identified by per image OD values indicative of the presence of hemoglobin, and cell volumes determined based on the amount of hemoglobin detected for a given RBC. The MCV value and the associated statistical values can be determined as indicated above, and the RDW subsequently determined.

Although this invention has been shown and described with respect to the detailed embodiments thereof, it will be understood by those skilled in the art that various changes in form and detail may be made without departing from the spirit and scope of the invention.

What is claimed:

1. A method for determining hemoglobin concentration of a blood sample, comprising:
   depositing an unlysed, substantially undiluted blood sample into an analysis chamber adapted to quiescently hold the sample for analysis, the chamber defined by an interior surface of a first panel, and an interior surface of a second panel, wherein both panels are transparent, and which chamber has a height extending between the interior surface of the first panel and the interior surface of the second panel;
   imaging the sample in a region of the analysis chamber where the height of the chamber is no more than about twenty microns (20μ) or no less than about two microns (2μ), to produce image signals representative of the optical density of the imaged region, which imaged sample includes non-red blood cell constituents;
   determining a sample representative optical density value using the image signals representative of the optical density of the sample within the imaged region; and
   determining the hemoglobin concentration of the sample using the sample representative optical density value.

2. The method of claim 1, wherein the image signals representative of the optical density of the imaged region are representative of optical density on a per image unit basis within the imaged region.

3. The method of claim 2, wherein the image unit is a pixel.

4. The method of claim 1, wherein the interior surface of the first panel and the interior surface of the second panel are substantially parallel each other.

5. The method of claim 1, wherein the chamber height is about four microns (4μ).

6. The method of claim 1, wherein the sample representative optical density value is determined using image signals created from a sample illuminator emitting light at a single peak wavelength.

7. The method of claim 6, wherein the determining the sample representative optical density value includes determining per image unit OD values in the region of the analysis chamber, and statistically analyzing the per image unit OD values to determine the sample representative optical density value.

8. The method of claim 6, wherein the determining the hemoglobin concentration of the sample includes directly or indirectly using empirical data with the sample representative optical density value to determine the hemoglobin concentration of the sample, which empirical data includes optical density values correlated to hemoglobin concentration values.

9. The method of claim 6, wherein the determining the hemoglobin concentration of the sample includes directly or indirectly using a theoretical model with the sample representative optical density value to determine the hemoglobin concentration of the sample.

10. The method of claim 6, wherein the determining the hemoglobin concentration of the sample includes directly or indirectly using an analytical model with the sample representative optical density value to determine the hemoglobin concentration of the sample.

11. The method of claim 1, wherein the determining the sample representative optical density value of the sample within the imaged region includes determining per image unit OD values of the sample within the region of the analysis chamber, and statistically analyzing the per image unit OD values to determine the sample representative optical density value.

12. The method of claim 11, wherein the determining the hemoglobin concentration of the sample includes directly or indirectly using empirical data with the sample representative optical density value to determine the hemoglobin concentration of the sample, which empirical data includes optical density values correlated to hemoglobin concentration values.

13. An apparatus for determining hemoglobin concentration within an unlysed, substantially undiluted whole blood sample, which sample includes non-red blood cell constituents, comprising:
   an analysis chamber configured to quiescently hold the sample for analysis, the chamber defined by an interior surface of a first panel, and an interior surface of a second panel, wherein both panels are transparent, and which chamber has a height extending between the interior surface of the first panel and the interior surface of the second panel, which height is no more than about twenty microns (20μ) or no less than about two microns (2μ);

a sample illuminator configured to emit light to pass through a region of the unlysed, substantially undiluted sample quiescently residing within the chamber, which region includes red blood cells and one or more non-red blood cells constituents;

an image dissector configured to capture light originating from the sample illuminator and passed through the sample, including the one or more non-red blood cell constituents, quiescently disposed within the chamber, and to produce image signals representative of the light passed through the sample; and an analyzer adapted to determine a sample representative optical density value using the image signals, and to determine the hemoglobin concentration of the region of the unlysed, substantially undiluted sample using the sample representative optical density value.

14. The apparatus of claim 13, wherein the analyzer is adapted to determine optical density values on a per image unit basis within the imaged region, and to determine the sample representative optical density value using the per image unit optical density values.

15. The apparatus of claim 14, wherein the analyzer is adapted to statistically analyze the per image unit OD values to determine the sample representative optical density value.

16. The apparatus of claim 13, wherein the sample illuminator is adapted to emit the light at a single peak wavelength, and the analyzer is adapted to determine the sample representative optical density value using image signals produced by the image dissector sensing the sample illuminator operating at the single peak wavelength.

17. The apparatus of claim 13, wherein the chamber height is about four microns ($4\mu$).

18. The apparatus of claim 13, wherein the analyzer is adapted to determine the hemoglobin concentration of the sample using empirical data and the sample representative optical density value.

19. A method for determining a red blood cell distribution width (RDW) of a blood sample, comprising:

depositing an unlysed, substantially undiluted blood sample into an analysis chamber adapted to quiescently hold the sample for analysis;

imaging the sample in a region of the analysis chamber to produce image signals representative of the optical density of the imaged region, which imaged sample includes non-red blood cell constituents;

determining a sample representative optical density value using the image signals representative of the optical density of the sample within the imaged region; and determining the RDW of the sample using the sample representative optical density value.

20. The method of claim 19, wherein the determining the RDW of the sample using the sample representative optical density value further comprises determining a cell volume value for each of a clinically acceptable number of red blood cells, a standard deviation of the determined red blood cell volumes, and a mean red blood cell volume value for the clinically acceptable number of red blood cells.

* * * * *